United States Patent
Gudeman

(10) Patent No.: US 11,502,669 B2
(45) Date of Patent: Nov. 15, 2022

(54) SUBTERAHERTZ MICROFABRICATED SPECTROMETER

(71) Applicant: Innovative Micro Technology, Goleta, CA (US)

(72) Inventor: Christopher S. Gudeman, Lompoc, CA (US)

(73) Assignee: Innovative Micro Technology, Goleta, CA (US)

( * ) Notice: Subject to any disclaimer, the term of this patent is extended or adjusted under 35 U.S.C. 154(b) by 407 days.

(21) Appl. No.: 16/888,879

(22) Filed: Jun. 1, 2020

(65) Prior Publication Data

US 2020/0388475 A1  Dec. 10, 2020

Related U.S. Application Data

(60) Provisional application No. 62/858,062, filed on Jun. 6, 2019.

(51) Int. Cl.
| | |
|---|---|
| *G01N 22/00* | (2006.01) |
| *H03H 9/64* | (2006.01) |
| *B82Y 20/00* | (2011.01) |

(52) U.S. Cl.
CPC ............... *H03H 9/64* (2013.01); *B82Y 20/00* (2013.01); *G01N 22/00* (2013.01)

(58) Field of Classification Search
CPC .... B82Y 20/00; G01N 22/00; G01N 33/0022; G01N 21/3581; H03H 9/64
See application file for complete search history.

(56) References Cited

U.S. PATENT DOCUMENTS

2014/0018028 A1* 1/2014 Lemkin ............... H03D 7/1441
455/313
2017/0223653 A1* 8/2017 Weitnauer ......... H04W 56/0045

\* cited by examiner

*Primary Examiner* — Abdullahi Nur
(74) *Attorney, Agent, or Firm* — Jaquelin K. Spong

(57) ABSTRACT

A microfabricated spectrometer uses at least one filter to discriminate the frequency components of an incoming RF signal. The filter center frequencies are chosen to correspond to wavelengths of target species which may be present in the gas, and radiating at a characteristic frequency.

20 Claims, 3 Drawing Sheets

SUBTERAHERTZ MICROFABRICATED SPECTROMETER

CROSS REFERENCE TO RELATED APPLICATIONS

This US nonprovisional Patent Application claims priority to U.S. Provisional Application Ser. No. 62/858,062, filed Jun. 6, 2019. This preceding application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to microfabricated wavelength detector/separator, as applied to a gas sensing application.

Gas sensors require high sensitivity and high specificity, two factors that are often in opposition, since a very sensitive system will likely be sensitive to many gasses. But high sensitivity is extremely important. For example, exposure to 1 part per million of carbon monoxide (CO) in the atmosphere will cause headaches in 10 minutes and irreversible brain damage 60 minutes. Chemical receptor systems that provide very high sensitivity to CO, often have a low level sensitivity to $CO_2$, which is far more abundant. Thus, distinguishing between harmful and benign gases is a problem, especially as detectors can lose sensitivity. Chemical receptor systems can become contaminated, which causes a loss in sensitivity and resulting in risk to personnel.

Gas sensors fall into several categories.
1) Chemical receptor for specific capture of the target molecule
2) Resonant beam structures to determine the mass of the molecule
3) Sensors that combust the target species and measure its exothermicity
4) Chemical Field Effect Transistors (Chem-FET)
5) Combinations of the above.

All of these to some extent share the following draw backs:
1) Contamination
2) Probable false readings (inaccuracy)
3) Low sensitivity
4) Low specificity What is needed is a low cost, compact, low loss, narrow band device to sense volatile, low molecular weight gases in the mmWave region of the electromagnetic spectrum.

SUMMARY

We describe here a microfabricated subterahertz wavelength discriminating device, i.e. a spectrometer, which can sense identifying radiation, such as the radiation emitted by a gaseous species. The microfabricated subterahertz spectrometer may employ a surface acoustic wave (SAW) filter, an amplifier and a detector for sensing the presence of identifying/indicator wavelengths in an RF signal. The radiation is first received by an antenna and downshifted by mixing with a local oscillator. The downshifted signal is then fed to at least one SAW filter.

This microfabricated spectrometer may be used to detect emission from excited state volatile gas molecules with extremely high accuracy. The device may be fabricated lithographically on a semiconductor substrate in a volume process at low cost.

The subterahertz spectrometer may use a plurality of SAW filters, amplifiers, detectors and ADCs, wherein the plurality of SAW filters are arranged in a filter bank such that their center frequencies and passbands are adjacent and slightly overlapping. When the radiation is within the passband of one of the SAW filters in the filter bank, the amplifier, detector and ADC provide a signal indicative of the intensity of the radiation at that wavelength.

Alternatively, a single SAW filter, amplifier, detector and ADC may be used and the wavelength of the local oscillator may be tuned, in order to sweep the intermediate frequency through a range overlapping the SAW filter passband. By monitoring the filter output as a function of local oscillator frequency, the emission wavelength can be determined.

In any case, when the wavelength is detected and compared to a list of known indicator wavelengths, the emitting species may be identified.

Accordingly, disclosed here is an subterahertz microfabricated spectrometer. The spectrometer may include an RF antenna that captures radiation in the sub-terahertz range, a sub-terahertz mixer with a local oscillator frequency of greater than 100 GHz, at least one filter coupled to the mixer, wherein the filter has a passband and center frequency associated with a target gas compound, and at least one power monitoring circuit that monitors the transmission through the at least one filter.

A method for detecting a gas component is also described. The method may include capturing radiation in the sub-terahertz range using an RF antenna to produce an RF signal, mixing the RF signal with a local oscillator having a frequency in the subteraHz range with a subteraHz mixer, to produce an intermediate frequency in the 1-100 GHz range, applying the intermediate frequency to at least one filter having a passband that includes a frequency indicative of the presence of a target gas compound, monitoring the level of transmission through the at least one filter with at least one power monitoring circuit.

These and other features and advantages are described in, or are apparent from, the following detailed description.

BRIEF DESCRIPTION OF THE DRAWINGS

Various exemplary details are described with reference to the following figures, wherein.

It should be understood that the drawings are not necessarily to scale, and that like numbers may refer to like features.

DETAILED DESCRIPTION

Figure 1:
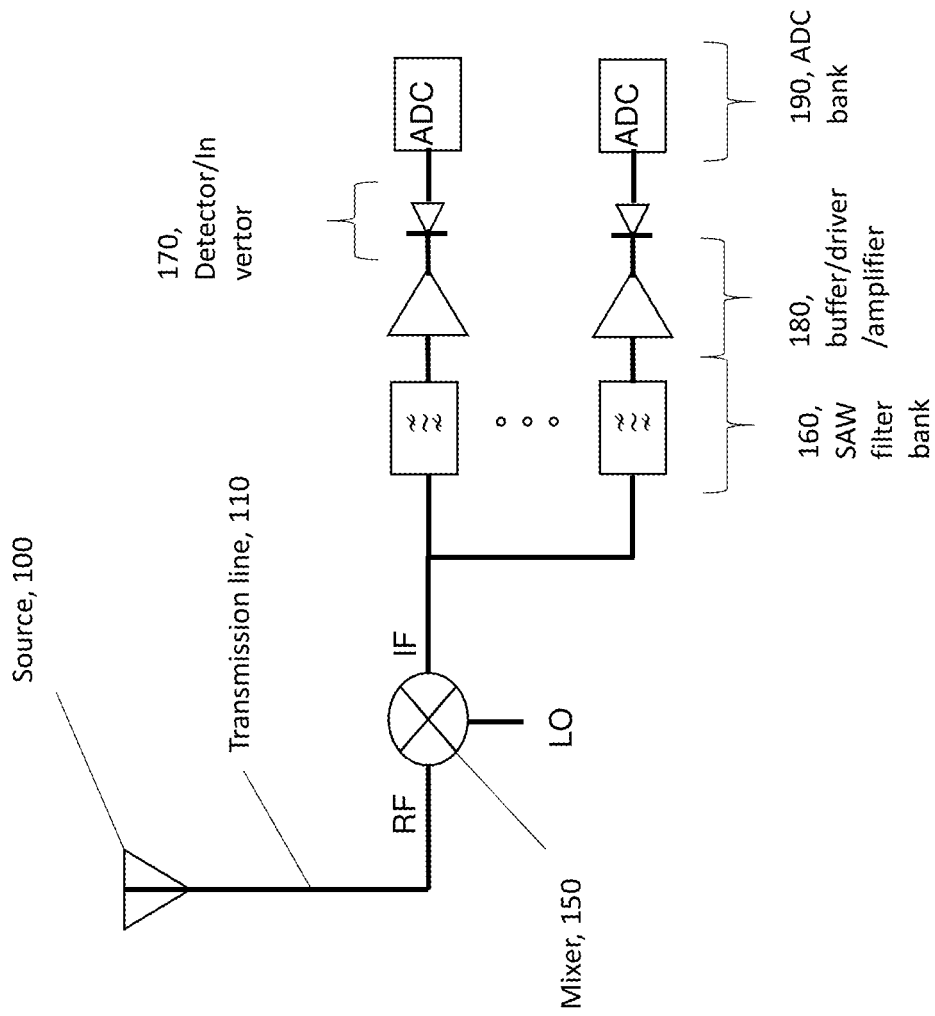
FIG. 1 is a schematic diagram of a first exemplary embodiment of a microfabricated subterahertz spectrometer.

This method uses a microfabricated architecture including microfabricated SAW filters and circuitry including an amplifier and detector.

An embodiment may include the following. An antenna with optimal performance near the frequency of interest is used to capture the radiation that naturally occurs from all polar gas molecules when they relax down to a lower rotation quantum state following a collision with another molecule, which excites them to a higher rotational quantum state. The intensity of this radiation increases with the frequency of the radiation. Thus high level quantum states, which are easily populated by collisions, produce radiation in 100-1000 GHz range, which provides relatively strong emission in a narrow line width that is relatively small compared to the frequency of emission.

Because sub-terahertz radiation is difficult to route and sense in conventional RF circuitry, a heterodyne down converter mixer is used. For example, for an emission line of 300 GHz, The Local Oscillator (LO) frequency of 302 GHz will create an Intermediate Frequency (IF) of 2 GHz. This IF is much easier to filter, amplify, and detect. This frequency can be detected with high signal to noise ratio (SNR) if the detection bandwidth is made narrow, to exclude other sources of RF power at neighboring frequencies. Surface Acoustic Wave (SAW) devices can provide very narrow passband filtering. Using multiple SAW filters with very closely spaced center frequencies can provide high SNR over many frequencies, allowing simultaneous detection of several different molecular species. Several closely packed SAW filters also provide a means of measuring the emission linewidth, which provides a measure of the gas pressure at the location of the emission. This can be useful for identifying gases at high altitude in the atmosphere.

As mentioned, different species of volatile gases may emit radiation at distinct and characteristic frequencies. These wavelengths are referred to herein as "indicator" wavelengths, because their detection indicates the presence of the particular gaseous species. If detected, the presence of this indicator radiation may suggest the presence of the volatile gas molecule.

The distinguishing feature of this microfabricated spectrometer is its ability to detect emission at particular wavelengths, with sufficient discrimination to identify the gaseous species. In the embodiments described here, the filtering function is accomplished by a bank of surface acoustic wave (SAW) filters. Each of the SAW filters in the bank has a unique passband, where radiation within the passband is transmitted by the filter and radiation outside the passband is blocked. If radiation within the passband is present, the radiation is transmitted through the device as a high signal and is then coupled to an amplifier. The output of the amplifier may be coupled to a detector which puts out the signal if a threshold level is reached. Following the detector, and analog to digital converter (ADC) may convert this signal voltage to a digital representation, for use in a controller or computer.

The following discussion presents a plurality of exemplary embodiments of the novel microfabricated spectrometer. The following reference numbers are used in the accompanying figures to refer to the following:

100 antenna receiving RF radiation
150 mixer
160 filter
170 detector/inverter
180 amplifier
190 ADC output A plurality of embodiments of the microfabricated subterahertz spectrometer are described below, using these reference numbers. The appended figures illustrate a number of different embodiment of this concept.

As used herein, the following terms may have the following meanings, which are consistent with usage by those skilled in the art. A stripline may be a transmission line trace surrounded by dielectric material suspended between two ground planes on internal layers of a PCB. A coplanar waveguide (CPW) may be is a type of electrical planar transmission line which can be fabricated using printed circuit board technology, and is used to convey microwave-frequency signals. On a smaller scale, coplanar waveguide transmission lines are also built into monolithic microwave integrated circuits. Conventional coplanar waveguide (CPW) consists of a single conducting track printed onto a dielectric substrate, together with a pair of return conductors, one to either side of the track. All three conductors are on the same side of the substrate, and hence are coplanar. The return conductors are separated from the central track by a small gap, which has an unvarying width along the length of the line. Away from the central conductor, the return conductors usually extend to an indefinite but large distance, so that each is notionally a semi-infinite plane.

An antenna may be a dipole or a plurality of dipoles, or it may be a horn that tapers from the opening that defines the crossectional capture area to the waveguide dimension that couples to the low noise amplifier. This antenna is designed to transmit or receive electromagnetic (e.g., TV or radio) waves at the frequency emitted by the target gas molecules.

A surface acoustic wave (SAW) filter is a filter whereby the electrical input signal is converted to a acoustic wave by so-called interdigital transducers (IDTs) on a piezoelectric substrate such as quartz or LiTaO3. The IDTs consist of interleaved metal electrodes which are used to launch and receive the waves, so that an electrical signal is converted to an acoustic wave and then back to an electrical signal.

The most common group of SAW-filters are bandpass filters, which are in very widespread use in radio systems (including mobile phone handsets and base stations) and in domestic TV. There are many types with differing advantages, such as low shape factor, low insertion loss, small size, or high-frequency operation. The wide variety of types is possible because almost arbitrary shapes can be defined on the surface with very high precision. SAW filters are limited to frequencies from about 50 MHz up to 3 GHz.

FIG. 1 illustrates a first embodiment of this microfabricated subterahertz spectrometer. FIG. 1 shows the source, 100, which may be an antenna, whose output is coupled to a mixer 150. The source may be an RF or microwave antenna for example, or some other receiver. The antenna 100 may receive broadcast radiation, and couples this radiation into a transmission line or waveguide 110. The frequency range of response of this antenna 100 may be in the range 300 GHz to 3 THhz, for example. The antenna may be a conductor shaped into a loop about 1' square. A horn may be used to collect the radiation. The transmission line 100 may be a coplanar waveguide (CPW), a stripline or a hollow rectangular metallic waveguide, for example. The transmission line 110 transmits this radiation as a traveling wave traveling along transmission line 110 to a mixer or a low noise amplifier 150.

The mixer may accept the signal from the antenna 100, and mix it with a local oscillator, as is done in standard much lower radio frequency devices. As a result of the mixing, a downshifted intermediate frequency (IF) may be created by the mixer. The useful frequency range for the downshifted intermediate frequency (IF) may be, for example, 100 MHz to 10 GHz, or more preferably, 1 GHz to 10 GHz. For example, if the frequency of interest is 2.1 GHz, a 300 GHz signal may be mixed with a 302 GHz local oscillator frequency, to produce a 2 GHz intermediate frequency.

This intermediate frequency may be coupled to a bank of SAW filters 160 as shown in FIG. 1. This bank of filters may comprise a plurality of SAW bandpass filters having a passband about 250 MHz wide. The center of the passband may be about 2 GHz from the center frequency of the adjacent SAW filter in the filter bank 160.

In addition to the bank of SAW filters, 160, there may be coupled to this filter bank, a bank of drivers/operational amplifiers 180. For example, if there are 50 amplifiers in the amplifier bank arranged all in parallel, the amplifiers 180(*x*) in the bank may be labelled 180(1), 180 (2) . . . 180(50), for example. Downstream of the amplifiers may further be a bank of diode detectors, 170. These components 170(*x*) where the 50 detectors may be labelled 170(1), 170(2) . . . 170(50), for example. Detector 170(*x*) will put out a HIGH signal when the threshold input from the amplifier 180(*x*) is also high.

Finally, a bank of analog-to-digital converters (ADCs) 190 may be coupled to the bank of detectors 170. There may be, for example, 50 ADCs, and thus there may be ADC 190(1) through ADC 190(50) corresponding to each of the elements of the detector bank 170, amplifiers 180, and SAW filters 160. For a 50-element bank, these components may be labelled 170(1), 170(2) . . . 170(50), 180(1), 180(2) . . . 180(50), 160(1), 160(2) . . . 160(50), and 190(1), 190(2) . . . 190(50) for the detectors, amplifiers, SAW filters, and ADCs respectively. Alternatively, a single ADC may be used to sample the voltage on sample-and-hold circuits that are deployed on each diode detector. This may provide for lower cost implementation.

For example, if the received signal from the source 100 has a component with a frequency at or near the center frequency of SAW filter 12, for example, in a bank of 50 SAW filters, and this filter center frequency is about 2.1 GHz, then the signal will pass through SAW filter 160(12) and to amplifier 170 (12). Detector 170(12) will then also go HIGH. The signal will finally be converted to a digital representation by ADC 190(12) for further use by a computer.

As an example, if the antenna is picking up a 301.5 GHz signal, and this signal mixed with a local oscillator having a frequency of 303 GHz, the radiation is downshifted to 2.5 GHz. This intermediate frequency is then fed to the filter bank having SAW passband filters spaced every 100 MHz from 1 to 5 GHz, the SAW filter 160 with its center frequency at about 2.5 GHz will transmit the signal when the local oscillator is at 303 GHz, from which it can be inferred that the radiation contains energy at 301.5 GHz.

Figure 2:
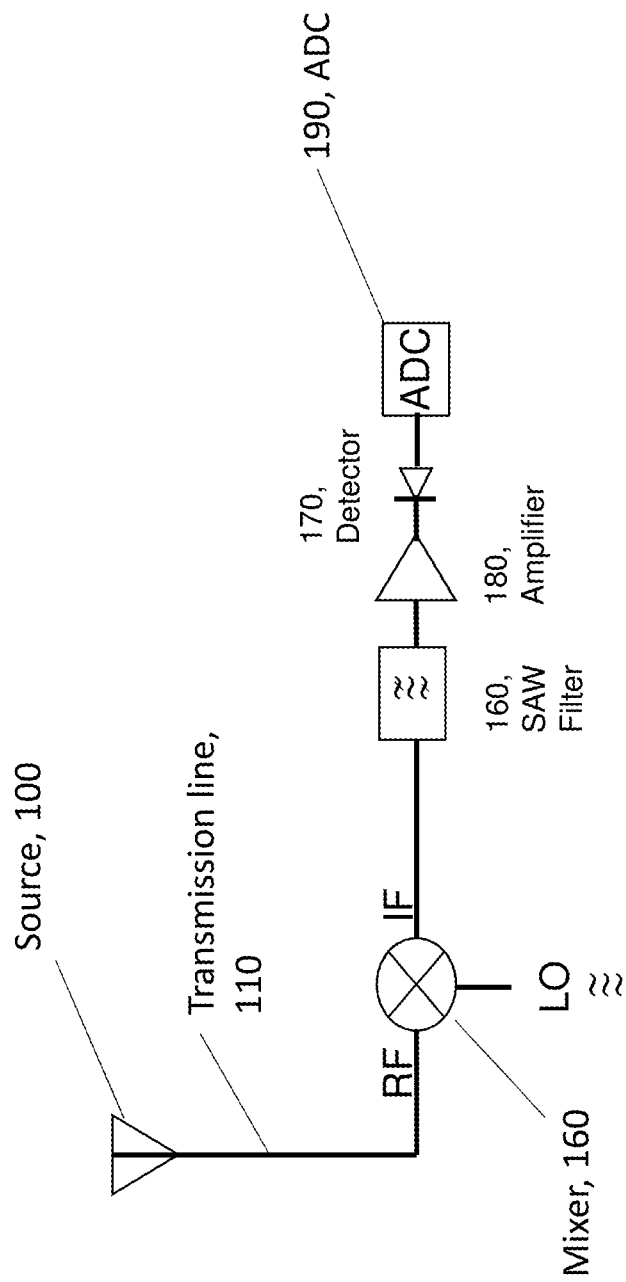
FIG. 2 is a schematic diagram of a second exemplary embodiment of a microfabricated subterahertz spectrometer.

FIG. 2 is another illustration of a second exemplary embodiment of microfabricated spectrometer. In this embodiment, rather than banks of filters, amplifiers, detectors and ADCs, just a single circuit including a single SAW filter, a single amplifier and a single detector may be used.

Similar to the first embodiment, a source 100, which may be an antenna, 100, may receive radio frequency broadcast radiation over the air, in the RF band. The antenna or source, 100, may again be coupled to a transmission line, strip line or coplanar waveguide 110. The signal received from the antenna, 100, will therefore be coupled into the strip line 110 where it may become a traveling wave in the waveguide or transmission line to the mixer 150.

The mixer may accept the signal from the source, and mix it with the local oscillator, as was done in the previous embodiment. As a result of the mixing, a downshifted intermediate frequency (IF) may be created by the mixer. For example, if the frequency of interest is 2.0 GHz, a 300 GHz signal may be mixed with a 302 GHz local oscillator frequency, to produce a 2 GHz intermediate frequency.

This intermediate frequency may be coupled to a SAW filter 160 as was shown in FIG. 1. The center of the passband of this filter may be about 2.1 GHz.

In addition to the SAW filter, 160, there may be coupled to this filter an operational amplifier 180. Downstream of this amplifier may further be a diode detector, 170.

Finally, a single analog-to-digital converter (ADCs) 190 may be coupled to the detector 170. In this embodiment, there may be only one ADC 190 corresponding to the single detector, and amplifier 180, and SAW filter 160.

In this embodiment, the frequency of the intermediate frequency IF may be swept through a range of frequencies by sweeping the local oscillator frequency. In one embodiment, a SAW filter is chosen which has a passband centered at 2.0 GHz as an indicator wavelength. If the antenna is picking up a 302 GHz signal, and the local oscillator is swept from 300 GHz to 310 GHz, the intermediate frequency is tuned from 1 to 9 GHz. The SAW filter 160 with its center frequency at about 2.0 GHz will transmit the signal when the local oscillator is at 303 GHz, from which it can be inferred that the radiation contains energy at 302 GHz.

Figure 3:
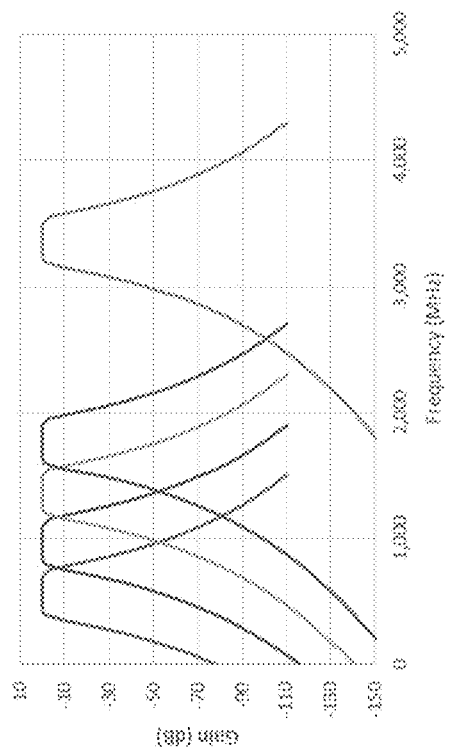
FIG. 3 is a graph showing the bandpass characteristics of the SAW filters.

FIG. 3 shows the passbands of a bank of SAW filters, such as those shown in FIG. 1. Although only 5 SAW passbands are shown, it should be understood that there may be many more filters in the filter bank. As shown in FIG. 3, each of the filters has a passband of about 1 GHz and a center frequency ranging from 500 MHz to 3.25 GHz.

Accordingly, disclosed here is a multichannel microfabricated subterahertz spectrometer. The spectrometer may include an RF antenna that captures radiation in the sub-terahertz range, a sub-terahertz mixer with a local oscillator frequency of greater than 100 GHz, at least one filter element coupled to the mixer, wherein the filter has a passband and center frequency associated with a target gas compound, and at least one power monitoring circuit that monitors the transmission through the at least one filter.

The at least one filter may include a bank or array of filters, each of which has a passband that is immediately adjacent to its neighbor. The at least one power monitoring circuit may comprise a bank of power monitoring circuits, with each power monitoring circuit in bank coupled to each filter element in the bank of filter elements.

The subterahertz mixer may mix the local oscillator with the signal captured by the antenna to produce a down shifted intermediate frequency in the passband of at least one of the at least one filter element.

The local oscillator may be tunable through a range of frequencies from about 100 GHz to 500 GHz. The at least one filter may be at least one SAW filter. The at least one power monitoring circuit may include at least one amplifier coupled to the at least one filter, and at least one detector coupled to the at least one amplifier. The at least one power monitoring circuit may further include at least one analog to digital converter coupled to the at least one detector.

The at least one amplifier, at least one detector and at least one analog-to-digital converter may each comprise a bank of amplifiers, detectors and analog-to-digital converters, wherein each of the banks of amplifiers, detectors and analog-to-digital converters is coupled to a corresponding one of the filters in the bank of filters. The filters may be SAW filters.

The subteraHertz spectrometer may further include a computer programmed to monitor the output of the at least one power monitoring circuit as a function of the frequency of the local oscillator, as it is tuned through a frequency band.

A method for detecting a gas component is also described, using the microfabraicated subteraHertz spectrometer. The method may include capturing radiation in the sub-terahertz range using an RF antenna to produce an RF signal, mixing the RF signal with a local oscillator having a frequency in the subteraHz range with a subteraHz mixer, to produce an intermediate frequency in the 1-100 GHz range, applying the intermediate frequency to at least one filter having a passband that includes a frequency indicative of the presence of a target gas compound, and monitoring the level of transmission through the at least one filter with at least one power monitoring circuit.

The at least one filter may comprises a bank or array of filters, each of which has a passband that is immediately adjacent to its neighbor; and wherein the at least one power monitoring circuit comprises a bank of power monitoring circuits, with each power monitoring circuit in bank coupled to each filter element in the bank of filter elements.

The subterahertz mixer may mix the local oscillator with the signal captured by the antenna to produce a down shifted intermediate frequency in the passband of at least one of the at least one filter element. The method may further include tuning the local oscillator through a range of frequencies from about 100 GHz to 500 GHz, and monitoring an output of the at least one SAW filter as a function of the frequency of the local oscillator, to identify a frequency component indicative of the presence of a target gas compound.

The at least one filter may comprise at least one SAW filter. The at least one power monitoring circuit may include at least one amplifier coupled to the at least one filter, and at least one detector coupled to the at least one amplifier. The power monitoring circuit may further include at least one analog to digital converter coupled to the at least one detector.

The at least one amplifier, at least one detector and at least one analog-to-digital converter may each comprise a bank of amplifiers, detectors and analog-to-digital converters, wherein each of the banks of amplifiers, detectors and analog-to-digital converters is coupled to a corresponding one of the filters in the bank of filters.

The filters may be SAW filters. The method may further comprise monitoring an output of the at least one power monitoring circuit as a function of the frequency of the local oscillator, as it is tuned through a frequency band.

While various details have been described in conjunction with the exemplary implementations outlined above, various alternatives, modifications, variations, improvements, and/ or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A multichannel microfabricated spectrometer, comprising:
    an RF antenna that captures radiation in the sub-terahertz range;
    a sub-terahertz mixer with a local oscillator frequency of greater than 100 GHz;
    at least one filter element coupled to the mixer, wherein the filter has a passband and center frequency associated with a target gas compound; and
    at least one power monitoring circuit that monitors the transmission through the at least one filter.

2. The multichannel microfabricated spectrometer of claim 1, wherein the at least one filter comprises an array of filters, each of which has a passband that is immediately adjacent to its neighbor; and wherein the at least one power monitoring circuit comprises a bank of power monitoring circuits, with each power monitoring circuit in bank coupled to each filter element in the bank of filter elements.

3. The multichannel microfabricated spectrometer of claim 1, wherein the subterahertz mixer mixes the local oscillator with the signal captured by the antenna to produce a down shifted intermediate frequency in the passband of at least one of the at least one filter element.

4. The multichannel microfabricated spectrometer of claim 1, wherein the local oscillator is tunable through a range of frequencies from about 100 GHz to 500 GHz.

5. The multichannel microfabricated spectrometer of claim 1, wherein the at least one filter comprises at least one SAW filter.

6. The multichannel microfabricated spectrometer of claim 1, wherein the at least one power monitoring circuit comprises:
    at least one amplifier coupled to the at least one filter, and
    at least one detector coupled to the at least one amplifier.

7. The multichannel gas sensor of claim 6, wherein the at least one power monitoring circuit further comprises:
    at least one analog to digital converter coupled to the at least one detector.

8. The multichannel microfabricated spectrometer of claim 7, wherein the at least one amplifier, at least one detector and at least one analog-to-digital converter each comprise a bank of amplifiers, detectors and analog-to-digital converters, wherein each of the banks of amplifiers, detectors and analog-to-digital converters is coupled to a corresponding one of the filters in the bank of filters.

9. The multichannel microfabricated spectrometer of claim 8, wherein the filters are SAW filters.

10. The multichannel microfabricated spectrometer of claim 8, further comprising:
    a computer programmed to monitor the output of the at least one power monitoring circuit as a function of the frequency of the local oscillator, as it is tuned through a frequency band.

11. A method for detecting a gas component, comprising:
    capturing radiation in the sub-terahertz range using an RF antenna to produce an RF signal;
    mixing the RF signal with a local oscillator having a frequency in the subteraHz range with a subteraHz mixer, to produce an intermediate frequency in the 1-100 GHz range;
    applying the intermediate frequency to at least one filter having a passband that includes a frequency indicative of the presence of a target gas compound;
    monitoring the level of transmission through the at least one filter with at least one power monitoring circuit.

12. The method for detecting a gas component of claim 11, wherein the at least one filter comprises an array of filters, each of which has a passband that is immediately adjacent to its neighbor; and wherein the at least one power monitoring circuit comprises a bank of power monitoring circuits, with each power monitoring circuit in bank coupled to each filter element in the bank of filter elements.

13. The method for detecting a gas component of claim 11, wherein the subterahertz mixer mixes the local oscillator with the signal captured by the antenna to produce a down shifted intermediate frequency in the passband of at least one of the at least one filter element.

14. The method for detecting a gas component of claim 11, further comprising:
tuning the local oscillator through a range of frequencies from about 100 GHz to 500 GHz, and monitoring an output of the at least one SAW filter as a function of the frequency of the local oscillator, to identify a frequency component indicative of the presence of a target gas compound.

15. The method for detecting a gas component of claim 11, wherein the at least one filter comprises at least one SAW filter.

16. The method for detecting a gas component of claim 11, wherein the at least one power monitoring circuit comprises:
at least one amplifier coupled to the at least one filter, and
at least one detector coupled to the at least one amplifier.

17. The method for detecting a gas component of claim 16, wherein the at least one power monitoring circuit further comprises:
at least one analog to digital converter coupled to the at least one detector.

18. The method for detecting a gas component of claim 17, wherein the at least one amplifier, at least one detector and at least one analog-to-digital converter each comprise a bank of amplifiers, detectors and analog-to-digital converters, wherein each of the banks of amplifiers, detectors and analog-to-digital converters is coupled to a corresponding one of the filters in the bank of filters.

19. The method for detecting a gas component of claim 11, wherein the filters are SAW filters.

20. The method for detecting a gas component of claim 11, further comprising:
monitoring an output of the at least one power monitoring circuit as a function of the frequency of the local oscillator, as it is tuned through a frequency band.

* * * * *